United States Patent [19]

Konrad et al.

[11] Patent Number: 4,603,048
[45] Date of Patent: Jul. 29, 1986

[54] ACID TENSIDE-ANION SOLUTION OF CHITOSAN AND ITS USE IN COSMETIC PREPARATIONS

[75] Inventors: Eugen Konrad, Darmstadt; Güenther Lang, Muehltal, both of Fed. Rep. of Germany

[73] Assignee: Wella Aktiengesellschaft, Darmstadt, Fed. Rep. of Germany

[21] Appl. No.: 431,573

[22] Filed: Sep. 30, 1982

[30] Foreign Application Priority Data

Oct. 9, 1981 [DE] Fed. Rep. of Germany ....... 3140134

[51] Int. Cl.$^4$ .......................... A61K 7/06; A61K 7/09
[52] U.S. Cl. ........................................ 424/70; 424/63; 424/71; 424/72
[58] Field of Search ............................. 536/20; 424/70

[56] References Cited

U.S. PATENT DOCUMENTS

| | | | |
|---|---|---|---|
| 3,879,376 | 4/1975 | Vanlerberghe et al. | 424/361 |
| 3,953,608 | 4/1976 | Vanlerberghe et al. | 424/73 |
| 4,031,025 | 6/1977 | Vanlerberghe et al. | 424/361 |
| 4,134,412 | 1/1979 | Gross et al. | 424/71 |

FOREIGN PATENT DOCUMENTS

| | | | |
|---|---|---|---|
| 870120 | 7/1949 | Fed. Rep. of Germany | 536/20 |
| 2627419 | 12/1977 | Fed. Rep. of Germany | 424/70 |
| 2754796 | 6/1979 | Fed. Rep. of Germany | 424/70 |

Primary Examiner—Dale R. Ore

Attorney, Agent, or Firm—Michael J. Striker

[57] ABSTRACT

Acid aqueous or aqueous-alcoholic solutions of a salt of chitosan, in which the anion of the salt is a tenside-anion of the general formula I

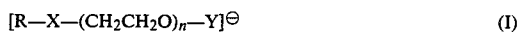

$$[R-X-(CH_2CH_2O)_n-Y]^\ominus \quad (I)$$

with R being $C_8$–$C_{30}$-alkyl or $C_8$–$C_{30}$-alkylene, X is O, COO, CONR' (R' is H, $C_1$–$C_4$-alkyl or $C_1$–$C_4$-hydroxyalkyl), phenoxy, n is 1 to 100, and Y is $(CH_2)_m COO^\ominus$ (m is 1 to 4) or $SO_3^\ominus$, as well as cosmetic preparations with a content of these solutions. The chitosan salt solutions are obtained by dissolving chitosan in an aqueous or aqueous-alcoholic solution containing, relative to the free amino groups of the chitosan, an about equimolar amount of a tenside of the formula II

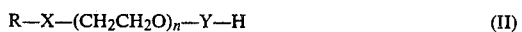

$$R-X-(CH_2CH_2O)_n-Y-H \quad (II)$$

in which R, X, n and Y have the above-given meanings. The chitosan salts contained in the solutions possess good film-forming characteristics of known chitosan salts, but in the presence of anionic tenside form no insoluble chitosan salts. The solutions can therefore be used as skin care, hair conditioning or hair strengthening component in cosmetic preparations, particularly also in shampoos on the basis of anionic tensides.

3 Claims, No Drawings

ACID TENSIDE-ANION SOLUTION OF CHITOSAN AND ITS USE IN COSMETIC PREPARATIONS

BACKGROUND OF THE INVENTION

Chitosan is a high polymer amino cellulose derivative and is capable of forming salts with acids. It is produced by alkaline entacetylation from chitin. The complete entacetylation is difficult, since the alkali enters into the chitin particles only incompletely during the reaction. A practically acetyl-free chitin, namely pure chitosan, can be obtained only through repeated alkali treatment or through fractionation. Commercial chitosan represents therefore a more or less entacetylated product with a chitosan portion from about 70 to 90% by weight.

The corresponding salts can be obtained by neutralization of the free amino groups of the chitosan with acids. Acids which provide the water-soluble salts of chitosan are, for example, hydrochloric acid, formic acid, acetic acid, lactic acid or other low molecular inorganic or organic acids.

The water-soluble salts of chitosan are used as additives in the paper and textile industries, as coagulants for suspensions and as chelating agents for heavy metals. In addition, several medicinal uses for water-soluble chitosan salts are known, for example as described in the book "Chitin" by Muzarelli, Pergamon Press, Oxford, 1977. Finally, the use of water-soluble chitosan salts, particularly since they have the character of cationic resins, as strengthening and conditioning components of hair treatment preparations, is known in the field of cosmetics. For example, their use in preparations for the strengthening of hairdos is known from German patent No. 2,627,419, whereas German Offenlegungsschrift No. 2,754,796 describes their employment in hair treatment and hair washing preparations. In aqueous or aqueous-alcoholic solutions of chitosan with the mentioned acids, there forms, however, in the presence of typical anionic tensides, such as e.g. alkylsulfates, alkylethersulfates, alkylsulfonates, alkylarylsulfonates, alkylsulfosuccinates and the alkali salts of long-chain fatty acids, insoluble chitosan salts. The valuable characteristics of chitosan can therefore not be utilized for preparations based upon such anionic tensides, such as for example textile and household cleaning preparations, personal hygiene (body) cleaning preparations, shampoos or hair conditioning preparations.

SUMMARY OF THE INVENTION

It is therefore an object of the present invention to make available aqueous or aqueous-alcoholic solutions of chitosan salts, with which, in the presence of typical anionic tensides, no insoluble chitosan salts are formed, and which therefore makes possible the inclusion of the chitosan also in anionic tenside-containing preparations.

It has been discovered that acid aqueous or aqueous-alcoholic solutions of a salt of chitosan, thereby characterized in that the anion of the salt is a tenside-anion of the general formula I $$[R-X-(CH_2CH_2O)_n-Y]^{\ominus} \quad (I)$$

in which R is a straight-chain or branched alkyl or alkylene group with 8 to 30 carbon atoms, X is one of the groups

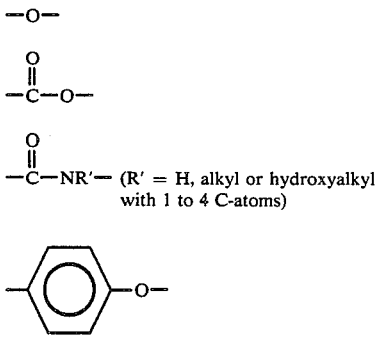

(R' = H, alkyl or hydroxyalkyl with 1 to 4 C-atoms)

n is a whole number from 1 to 100, preferably 4 to 20, and Y is one of the groups $-(CH_2)_m COO^{\ominus}$ (m = 1 to 4)
$-SO_3^{\ominus}$ fulfill the objective according to the present invention.

The solutions according to the present invention are obtained, for example, as follows:

According to one particular embodiment, the chitosan is dissolved in an aqueous or aqueous-alcoholic solution containing relative to the free amino groups of the chitosan an about equimolar amount of a tenside of the formula II $$R-X-(CH_2CH_2O)_n-Y-H \quad (II)$$

in which R, X, n and Y have the above-given meaning.

According to another embodiment, an about equimolar amount, relative to the free amino groups of the chitosan, of a salt of the formula III $$[R-X-(CH_2CH_2O)_n-Y^{\ominus}]M^{\oplus} \quad (III)$$

in which R, X, n and Y have the above-given meanings and $M^{\oplus}$ is an alkali, ammonium or alkanol-ammonium ion, is added to an aqueous or aqueous-alcoholic solution of a salt of chitosan with a low molecular inorganic or organic acid.

For the production of the solutions according to the present invention following the second embodiment, suitable salts of chitosan with lower inorganic or organic acids are, for example, salts of chitosan with hydrochloric acid, formic acid, acetic acid, lactic acid, tartaric acid, citric acid and succinic acid.

Suitable tensides of the formula II for production of the chitosan salt solutions according to the present invention are, for example, fatty alcohol polyglycolether carboxylic acids of the formula R—O—(C₂H₄O)-n—COOH, alkylphenolpolyglycolether carboxylic acids of the formula R—C₆H₄—O—(C₂H₄O)n—CH-2—COOH (in particular with R being octyl, nonyl), fatty alcohol polyglycolether sulfonic acids of the formula R—O—(C₂H₄O)n—SO₃H as well as fatty alkylamidopolyglycolethersulfate of the formula RCONR'—(C₂H₄O)n—SO₃H, in which R and R' have the above-given meaning and n is preferably from 4 to 20. For the utility according to the present invention, particularly suitable tensides are, for example, the products sold under the commercial designation AKYPO by the firm Chem-Y, Bodegraven, the Netherlands, such as laurylalcohol-polyglycolether carboxylic acid with an average 4.5 ethyleneoxide groups per molecule (AKYPO RLM 45), with 10 ethyleneoxide groups in the molecule (AKYPO RLM 100), with 13 ethyleneoxide groups in the molecule (AKYPO RLM 130), and with 16 ethyleneoxide groups in the molecule (AKYPO RLM 160). A further example is the compound cetyl alcohol polyglycolether carboxylic acid with 8 ethylene oxide groups in the molecule (AKYPO RCS 80).

Particularly suitable are cocos fatty acid amide polyglycolether sulfates, those with 10 ethyleneoxide groups in the molecule being preferred.

The chitosan to be used for production of the solutions can be provided in pure form or also be a typical commercial, partially entacetylated, product, in which the portion of free amino groups in the chitosan generally lies between about 70 and 90%.

The chitosan salt contained in the aqueous or aqueous-alcoholic solution from chitosan and a tenside of formula II can in principle be present in the solutions in any optional amount. However, on the basis of solubility, a content from 0.05 up to 10.0% by weight of the chitosan salt, relative to the amount of employed chitosan, is preferred.

Coming into consideration as alcohol for the production of the aqueous-alcoholic solutions are, in particular, all low molecular aliphatic uni- or multi-valent alcohols. Corresponding alcohols, suitable for a cosmetic utility, are for example ethanol, n-propanol, i-propanol, ethyleneglycol, 1,2-propyleneglycol, 1,3-propyleneglycol and glycerin.

The here-described aqueous or aqueous-alcoholic solutions of chitosan salts can be employed as film-forming component with excellent skin care and hair conditioning characteristics in cosmetic preparations. The chitosan salts display the outstanding characteristics of the simple chitosan salts described in German Offenlegungsschrift No. 2,754,796 and in German patent No. 2,627,419, but can, however, in contrast to the there-described salts, also be used together with known and typical anionic tensides, such as for example alkylsulfates, alkylethersulfates, alkylsulfonates, alkylarylsulfonates, alkylsulfosuccinates and salts of fatty acids. In addition to these and other known anionic tensides, also an excess, above the amount necessary for salt formation with chitosan, of a tenside of the general formula II, can serve. In the presence of anionic tensides, generally stable, clear solutions or disperse-cloudy preparations are obtained.

The chitosan salt solutions according to the present invention can therefore be used in all cosmetic preparations in which their film-forming, hair conditioning and skin care characteristics are desirable. Such cosmetic preparations include, for example hair care, hair rinse and hair wash preparations, shower gels, hair setting agents, color setting agents, shading agent and spray setting agents. Accordingly, such cosmetic preparations with a content of the above-described chitosan salt solutions are also within the scope of the present invention.

The chitosan salt solutions as well as cosmetic preparations containing them, display a pH-value in the acid range, particularly in the range from 2 to 6. The cosmetic preparations should contain the chitosan salt solution in an amount which is sufficient in order to effect a skin care activity, a hair conditioning activity, or an increase in the mechanical strength of the hair. This is generally the case with a content of chitosan salt from about 0.01 up to 5.0% by weight, relative to the amount of employed chitosan in the cosmetic preparation.

Aside from the new chitosan salt solutions according to the present invention, the preparations can, if necessary, additionally contain other cosmetic resins, such as for example polyvinylpyrrolidone, vinylpyrrolidone/vinylacetate mixed polymerizates as well as mixed and graft polymers of vinyl acetate and an unsaturated carboxylic acid, such as crotonic acid. As tenside, the preparations according to the present invention can contain, in addition to anionic tensides, also non-ionic, cationic or amphoteric tensides. With preparations in shampoo form, the total concentration of tenside generally amounts to between 5 and 50% by weight.

The cosmetic preparations according to the present invention can in other respects obviously contain all customary components normally used in cosmetics, such as thickening agents, for example fatty acid alkanolamide, carboxymethylcellulose, hydroxymethylcellulose, esters of polyols with longer-chain and natural rubber materials, preservatives such as methyl-p-hydroxybenzoate and formaldehyde as well as moreover dyes, pigments and perfume oils or also lower molecular inorganic or organic salts such as NaCl, $Na_2SO_4$ or sodium acetate. It is likewise possible to spray these preparations from a pressure container with the aid of an atomizer or other suitable spray arrangement or in mixture with typical propellant gas.

The novel features which are considered characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

I. EXAMPLES FOR THE PRODUCTION OF CHITOSAN SALT SOLUTIONS

EXAMPLE 1

3.77 g of 80% entacetylated chitosan are dissolved in a solution of 11.32 g lauryl alcohol polyglycolether carboxylic acid with 16 ethylene oxide groups in the molecule (AKYPO RLM 160) in a mixture of 9.43 g isopropanol and 75.48 g water, with stirring. 100 g of a viscous, clear, aqueous-alcoholic chitosan salt solution with a pH of 3.6 are obtained.

EXAMPLE 2

2.0 g of 80% entacetylated chitosan are dissolved in a solution composed of 10.0 g lauryl alcohol polyglycolether carboxylic acid with an average 4.5 ethylene oxide groups per molecule (AKYPO RLM 45), 0.5 g polyoxyethylene glycerin-monoisostearate (commercial product TAGAT I of the firm Goldschmidt, Essen) and 73.3 g water, with stirring. 100 g of a clear, acid aqueous-alcoholic chitosan salt solution are obtained.

EXAMPLE 3

0.53 g of 80% entacetylated chitosan is dissolved in a mixture composed of 6.2 g cetyl alcohol polyglycolether carboxylic acid with 8 ethylene oxide groups in the molecule (AKYPO RCS 80), 0.53 g isopropanol, 0.26 g polyoxyethylene glycerin-monoisostearate (commercial product TAGAT I of the firm Goldschmidt, Essen) and 39.68 g water. After the addition of 52.80 g isopropanol to the obtained cloudy solution, 100 g of a clear, acid aqueous-alcoholic chitosan salt solution are produced.

EXAMPLE 4

4.0 g of 80% entacetylated chitosan are dissolved in a solution composed of 12.0 g lauryl alcohol polyglycolether carboxylic acid with 10 ethylene oxide groups in the molecule (AKYPO RLM 100), and 84.2 g water, with slight heating. After filtering off insoluble particles, 100 g of a clear aqueous chitosan salt solution, displaying a pH-value of 4.1 are obtained.

EXAMPLE 5

A solution composed of 10 g of the sodium salt of cocos fatty acid amide polyglycolethersulfate with 10 ethylene oxide groups in the molecule, in 75 g water, is adjusted with hydrogen chloride to a pH of 2.0. 20 g isopropanol are added to this solution. Then, under stirring, 2.0 g of 80% entacetylated chitosan are dissolved in the solution. After filtering off the small amounts of insoluble component, a clear, acid aqueous-alcoholic chitosan salt solution is obtained.

The solution can also be obtained by dissolving 2.0 g of 80% entacetylated chitosan in 75.0 g of a 0.02 molar aqueous hydrogen chloride solution. 20.0 g isopropanol are added to the solution. Finally, 10.0 g of the sodium salt of cocos fatty acid amide polyglycolethersulfate, with 10 ethylene oxide groups in the molecule, are dissolved, under stirring, in the aqueous-alcoholic solution of chitosan hydrochloride. The insoluble portion is filtered off.

II. EXAMPLES FOR COSMETIC PREPARATIONS

EXAMPLE A: Clear Shampoo

A mixture composed of 50 g of a solution according to Example 1, 11.2 g lauryl alcohol polyglycolether carboxylic acid with 4.5 ethylene oxide groups per molecule (AKYPO RLM 45), 0.2 g perfume oil and 0.1 g dye, is adjusted with a 10% aqueous caustic soda solution to a pH-value of 4.0. One obtains a clear shampoo with good wash and care characteristics.

EXAMPLE B: Cloudy Shampoo 60 g of a chitosan salt solution according to Example 1 are admixed, under stirring, with 40 g of a 28% aqueous solution of sodium lauryl polyglycolethersulfate, with average 2.5 ethylene oxide groups per molecule. After the addition of 5.5 g sodium hydroxide, the initially produced sediment dispersion is dissolved. With the addition of 0.1 g perfume oil, 0.05 g of a dye and 1.0 g of a turbidity agent, a shampoo is obtained which displays good wash characteristics, and imparts luster to the hair and a good combability as well as a good feel.

EXAMPLE C: Clear Hair Rinse

In 96.0 g of a chitosan salt solution according to Example 4, 3 g sodium chloride, 0.5 g perfume oil, and 0.5 g dye are dissolved. The obtained clear hair rinse preparation is used after washing the hair, and imparts to the hair, after rinsing off with water and drying, a good combability. The hairdo has, at the same time, obtained a more relaxed stability.

EXAMPLE D: Gel-form Hair Strengthener

A mixture, composed of 15.0 g of an aqueous chitosan salt solution according to Example 4, 6.0 g of a 50% aqueous solution of a copolymerisate of 20% polyvinylpyrrolidone/80% vinylacetate, 78.5 g isopropanol, 0.4 g perfume oil, and 0.1 g dye, is heated in a vessel for 30 minutes to a temperature of 50° C.

One obtains a gel-form hair strengthener, which liquefies when it is massaged into wet hair and displays excellent strengthening and care characteristics.

All of the percentages given above represent percent by weight.

It will be understood that each of the elements described above, or two or more together, may also find a useful application in other types of solutions differing from the types described above.

While the invention has been illustrated and described as embodied in tenside-anion solutions of chitosan and their use in cosmetic preparations, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A cosmetic preparation for conditioning of the hair and care of the skin comprising an amount which is sufficient in order to effect a skin care activity or an increase in the mechanical strength of the hair of an acid aqueous or aqeous-alcoholic solution of a salt of chitosan, with a content of chitosan salt from 0.01 to 5.0% by weight, relative to the amount of employed chitosan, in which the anion of the salt is a tenside anion of the general formula I

in which R is a straight-chain or branched alkyl or alkylene group with 8 to 30 carbon atoms, X is one of the groups

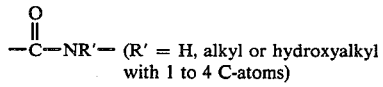

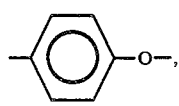

n is a whole number from 1 to 100, and Y is one of the groups

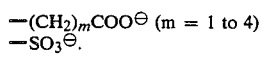

2. The cosmetic preparation according to claim 1, wherein the tenside-anion is selected from the group consisting of anions of fatty alcohol polyglycolether carboxylic acids of the formula R—O—($C_2H_4O$)$_n$—$CH_2$—COOH, aklylphenolpolyglycolether carboxylic acids of the formula R—$C_6H_4$—O—($C_2H_4O$)$_n$—$CH_2$—COOH, fatty alcohol polyglycolether sulfonic acids of the formula R—O—($C_2H_4O$)$_n$—$SO_3H$ and fatty alkylamidopolyglycolethersulfate of the formula RCONR'—($C_2H_4O$)$_n$—$SO_3H$, in which R and R' have the above given meaning and n is a number from 4 to 20.

3. The cosmetic preparation according to claim 1, wherein the tenside-anion is selected from the group consisting of anions of laurylalcohol polyglycolether carboxylic acid with an average of 4.5 ethyleneoxide groups per molecule, with 10 ethyleneoxide groups per molecule, with 13 ethyleneoxide groups per molecule, with 16 ethyleneoxide groups per molecule, cetyl alcohol polyglycolether carboxylic acid with 8 ethyleneoxide groups per molecule and cocos fatty acid amide polyglycolether sulfate with 10 ethyleneoxide groups per molecule.

* * * * *